United States Patent [19]
Watanabe et al.

[11] Patent Number: 5,516,640
[45] Date of Patent: May 14, 1996

[54] METHOD OF DETERMINATION OF PIVKA

[75] Inventors: Keisuke Watanabe, Ibaraki; Toru Naraki, Chiba; Yoshihiro Iwasaki, Tokyo, all of Japan

[73] Assignee: Eisai Co., Ltd., Tokyo, Japan

[21] Appl. No.: 229,280

[22] Filed: Apr. 18, 1994

[30] Foreign Application Priority Data

May 7, 1993 [JP] Japan .................................. 5-130015
Feb. 10, 1994 [JP] Japan .................................. 6-016348

[51] Int. Cl.$^6$ ..................... G01N 33/543; G01N 33/573; G01N 33/577
[52] U.S. Cl. ..................... 435/7.4; 435/7.94; 435/13; 436/518; 436/548; 436/811
[58] Field of Search ............. 435/7.4, 7.9, 7.92, 435/7.94, 7.95, 70.21, 240.26, 13, 973; 436/811, 518, 548

[56] References Cited

U.S. PATENT DOCUMENTS 4,353,982 10/1982 Gomez et al. .................... 435/962
4,780,410 10/1988 Matsuda et al. .................... 435/7.4

FOREIGN PATENT DOCUMENTS 142634 11/1989 European Pat. Off. .

OTHER PUBLICATIONS

Motohara, K., et al. "Detection of Vitamin K Deficiency . . . ", Pediatric Research, vol. 19, No. 4, 1985, pp. 354–357.
Okuda, H., et al. "Production of abnormal prothrombin . . . ", Journal of Hepatology, 1987; 4: 357–363.
Yoshikawa, Y., et al. "The Acquired Vitamin K–Dependent . . . ", Hepatology, vol. 8, No. 3, pp. 524–530, 1988.
Furukawa, M., et al. Kansaibogan ni okeru . . . , Kanzo, 1990; 31: P110.
Blanchard, R. A. et al. "Acquired Vitamin K–Dependent Carboxylation Deficiency in Liver Disease", The New England Journal of Medicine, 305(5) Jul. 30, 1981, pp. 242–248.
Soulier, J.–P., et al. "A New Method to Assay Des–γ–carboxyprothrombin", Gastroenterology, 1986;91:1258–62.
Kohler, G., et al. "Derivation of specific antibody–producing tissue culture . . . ", Eur. J. Immunol., 1976. 6:511–519.
Nelsestuen G. L. "Vitamin K–Dependent Plasma Proteins." Methods in Enzymology 107:507–516, 1984.
Bray, G. L. et al. "Calcium–Specific Immunoassays for Factor IX: Reduced Levels of Antigen in Patients with Vitamin K Disorders." J. Lab. Clin. Med. 107(3) 269–278, 1986.

*Primary Examiner*—David Saunders
*Attorney, Agent, or Firm*—Flynn, Thiel, Boutell & Tanis

[57] ABSTRACT

To provide a simple immunochemical assay of a PIVKA of every kind (PIVKA-VII, -IX, -X, -C, -S or -Z: protein induced by vitamin K absence) corresponding to a vitamin K-dependent protein. It has been confirmed that a PIVKA of every kind can be determined according to the double antibody sandwich method wherein use is made of a solid-supported anti-PIVKA-II monoclonal antibody. There is also disclosed a reagent for determination of a PIVKA of every kind according to the above-mentioned method.

1 Claim, 2 Drawing Sheets

METHOD OF DETERMINATION OF PIVKA

FIELD OF INDUSTRIAL APPLICATION

The present invention relates to The immunochemical assay of a PIVKA of every kind present in an organic specimen and a reagent therefor, which are utilized in the medical field.

PRIOR ART

Vitamin K-dependent plasma proteins present in organisms include prothrombin, factor VII, factor IX, factor X, protein C, protein S, and protein Z. According to biosynthesis mechanisms of these proteins, a precursor protein is carboxylated at the γ-positions of about 10 glutamic acid residues thereof in the presence of vitamin K and a carboxylase to be converted into an active-form normal protein, which manifests the physiological action thereof. These glutamic acid residues are present in the N-terminal region, which is referred to as the "Glaregion." In a state of physiological or clinical deficiency of vitamin K or in a state of suppressed action of vitamin K through administration of a vitamin K antagonist, proteins with incomplete carboxylation of those glutamic acid residues are formed.

"PIVKA" is a generic term for those vitamin K-dependent plasma proteins with such incomplete carboxylation, and is an abbreviation of "Protein Induced by Vitamin K Absence or Antagonist." The number of noncarboxylated residues among the about 10 glutamic acid residues present in the amino-terminal region is not fixed. Thus, one kind of protein is composed of several kinds of PIVKA compounds present in mixture.

PIVKA can also be said to be a protein wherein some γ-carboxyglutamic acid residues of the normal vitamin K-dependent plasma protein are descarboxylated. PIVKAs corresponding to the above-numerated vitamin K-dependent plasma proteins are referred to as PIVKA-II, PIVKA-VII, PIVKA-IX, PIVKA-X, PIVKA-C, PIVKA-S, and PIVKA-Z, respectively. PIVKA-II is a PIVKA of prothrombin.

The clinical usefulness of the determination of PIVKA is that PIVKA is produced in blood as a result of the above-mentioned incomplete γ-carboxylation in a state of vitamin K deficiency or suppression. Thus, the determination of PIVKA as a marker of the state of vitamin K deficiency or suppression is of clinical importance. It has recently been found out that various PIVKAs are produced in blood as a result of hepatocellular carcinoma. Since PIVKA-II is very often produced in patients with hepatocellular carcinoma who are negative for α-fetoprotein, which has been believed to be a good marker for hepatocellular carcinoma, it is recognized that clinical usefulness of PIVKA-II is equal to that of α-fetoprotein. The following publications (1) to (4) report on the relationship between various PIVKAs and vitamin K and hepatocellular carcinoma.

(1) Motohara K., Kuroki Y., Kan. H., Endo F., Matsuda I.

Detection of vitamin K deficiency by use of an enzyme-linked immunosorbent assay for circulating abnormal prothrombin. Pediatric Research. ]1985: 19:354–7

(2) Okuda H., Obata H., Nakanishi T., Furukawa R., Hashimoto E.

Production of abnormal prothrombin (des-γ-carboxyprothrombin) by hepatocellular carcinoma. Journal Hepatology. 1987; 4: 357–63

(3) Yoshikawa Y., Sakaa, Toda G.. Oka. H.

The acquired vitamin K-dependent γ-carboxylarion deficiency in hepatocellular carcinoma involves not only prothrombin, but also protein C. Hepatology. 1988; 8:524–530

(4) Furukawa M., Nakanishi T., Okuda H., Obata H., Suzuki K., Nishioka J.

Kansaiboaan ni okeru kakushu PIVKA no sansei ni kansuru kento (Investigations on production of various PIVKAs in hepatocellular carcinoma). Kanzo. 1990; 31: 110

Several methods of determination of various PIVKXs have been reported to date. Reported methods include competitive radioimmunoassay wherein use is made of a polyclonal anti-PIVKA-II antibody (Blanchard R. et. al., Acquired vitamin K-dependent carboxylation deficiency in liver disease. The New England Journal of Medicine. 1981; 305: 242–8) and a method wherein the thrombin activity of PIVKA-II remaining after absorption of normal prothrombin is measured (Soulief J. et. al. A new method to assay des-γ-carboxyprothrombin. Gastroenteroloay. 1986; 91: 1258–62). As for determination of PIVKA-IX, PIVKA-C, PIVKA-S and PIVKA-Z other than PIVKA-II, a method has been reported wherein barium chloride was added to a biological sample to precipitate normal proteins corresponding to the PIVKAs and the resulting supernatant used as a specimen from which the PIVKAs were determined according to sandwich EIA wherein use was made of antifactor IX polyclonal antibody, antiprotein C antibody, antiprotein S antibody and antiprotein Z antibody [Furukawa M. et. al., Kansaibogan ni okeru kakushu PIVKA no sansei ni kansuru kento (Investigations on production of various PIVKAs in hepatocellular carcinoma). Kanzo. 1990; 31: 110]. Further, Yoshikawa et. al. carried out the quantitative determination of PIVKA-C by calculating a ratio of The amount of normal protein C to The total amount of protein C while using a monoclonal antibody only reactive with normal protein C but non-reactive with PIVKA-C and concluded that The lower the ratio, the larger the amount of PIVKA-C (Yoshikawa Y. et. al., The acquired vitamin K-dependent γ-carboxylation deficiency in hepatocellular carcinoma involves not only prothrombin, but also protein C. Hepatology. 1988: 8: 524–0).

As is apparent from the foregoing reported examples, all of the methods are not practical in institutions, where a large number of clinical specimens are dealt with, because they need a pretreatment of a biological sample, involve intricate preparation of an antibody material for use in determination and/or a complicated system of determination. In contrast to these methods, a specific method of determination of PIVKA-II wherein use is made of an anti-PIVKA-II monoclonal antibody (EP-B 142 634) is very simple and characterized in that a large number of specimens can be subjected to accurate determination. Thus, a reagent for the determination according to this method is now widely used as the only diagnostic reagent for determination of PIVKA-II.

The anti-PIVKA-II monoclonal antibody MU-3 as disclosed in EP-B 142 634 is prepared by purifying PIVKA-II obtained from the blood plasma of a subject to which a vitamin K antagonist has been administered and immunizing mice with the purified PIVKA-II as an immunizing antigen. It may theoretically be possible to purify various PIVKAs other than PIVKA-II obtained From the blood plasma of a subject to which a vitamin K antagonist has been administered and using the same as immunizing antigens to immunize mice therewith to produce monoclonal antibodies against such various PIVKAs. Since, however, these various PIVKAs are actually contained only in very minute amounts in the blood plasma of a subject to which a vitamin K antagonist has been administered, a large amount of the blood plasma is necessary for producing the monoclonal antibodies using these PIVKAs, purification of which is very difficult.

As described above, only the method of determination of PIVKA-II, among various PIVKAs, was established as a practical method of accurate determination. Accordingly, establishment of an effective method of determination of every other PIVKA is strongly desired from research and clinical institutions.

SUMMARY OF THE INVENTION

An object of the present invention is to establish a simple and accurate immunochemical assay of PIVKA-VII, -IX, -X, -C, -S and -Z and apply thereto a reagent for diagnosis of hepatocellular function and pathology.

The inventors of the present invention have made an investigation into an epitope site of the anti-PIVKA-II monoclonal antibody MU-3 as disclosed in EP-B 142 634. More specifically, peptide fragments having various lengths have been synthesized based on the amino acid sequence of the Gla region of PIVKA-II, and the above-mentioned monoclonal antibody has been examined as to its capability of binding to these synthesized peptide fragments to find out that the epitope site for the above-mentioned antibody, is a descarboxypeptide located at the 13—to 23-positions of the amino acid sequence of prothrombin.

The comparison of the amino acid sequences of the Gla regions of the vitamin K-dependent plasma proteins with one another have revealed that as shown in Table 1 they are homologous and that their amino acid sequences located at the 13—to 21-positions in particular are highly homologous. This suggests a possibility that the other PIVKAs might be reactive with the above-mentioned anti-PIVKA-II monoclonal antibody. As a result of intensive investigations based on an idea of possible determinability of every individual PIVKA and or all PIVKAs in total, it has been found out for the first time that the abovementioned monoclonal antibody has a capability of unexpectedly strongly binding to PIVKA-VII, -IX, -X, -C, etc. The present invention has been completed based on such findings.

TABLE

Amino Acid Sequences of Gla Regions of Various PIVKAs

|       | 1   | 10         | 20          | 30          | 40        |
|-------|-----|------------|-------------|-------------|-----------|
| h-PT  | ANT—FLZZVRKGNLZRZC V ZZTCSYZZ A FZALZS S TATDVFW |
| h-FX  | ANS—FLZZMKKGHLZRZCMZZTCSYZZAR ZVFZDSDKTN ZFW |
| h-FIX | YN S G KL ZZFVQGNLZRZCMZZKCSFZZAR ZVEZNTZKTT ZFW |
| h-FVII| AN—AFLZZLRP G S LZRZCK ZZQCSFZZAR Z I FKDAZRTKLFW |
| h-PC  | ANS—FLZZL RH S S LZRZC I ZZ I CDFZZAKZ I FQNVDDTLAFW |
| h-PS  | ANS—LLZZTKQGNLZRZC I ZZLCNKZZARZVFZNDPZTD YFY |
| h-PZ  | AG S YLLZZLFZGNLZKZCY ZZ I CVYZZARZVFZNDZVTDZFW | h,human; PT,prothrombin; FX,factor X; FIX,factor IX; FVII,factor VII; PC,protein C; PS, protein S; PZ, protein Z; Z, γ-carboxylglutamic acid The above shown sequences are shown more in detail:

SEQ ID NO: 1
h-PT(Ala Asn Thr Phe Leu Xaa Xaa Val Arg Lys Gly Asn
Leu Xaa Arg Xaa Cys Val Xaa Xaa Thr Cys Ser Tyr
Xaa Xaa Ala Phe Xaa Ala Leu Xaa Ser Ser Thr Ala
Thr Asp Val Phe Trp)

SEQ ID NO: 2
h-FX(Ala Asn Ser Phe Leu Xaa Xaa Met Lys Lys Gly His
Leu Xaa Arg Xaa Cys Met Xaa Xaa Thr Cys Ser Tyr
Xaa Xaa Ala Arg Xaa Val Phe Xaa Asp Ser Asp Lys
Thr Asn Xaa Phe Trp)

SEQ ID NO: 3
h-FIX(Tyr Asn Ser Gly Lys Leu Xaa Xaa Phe Val Gln Gly
Asn Leu Xaa Arg Xaa Cys Met Xaa Xaa Lys Cys Ser
Phe Xaa Xaa Ala Arg Xaa Val Glu Xaa Asn Thr Xaa
Lys Thr Thr Xaa Phe Trp)

SEQ ID NO: 4
h-FVII(Ala Asn Ala Phe Leu Xaa Xaa Leu Arg Pro Gly Ser
Leu Xaa Arg Xaa Cys Lys Xaa Xaa Gln Cys Ser Phe
Xaa Xaa Ala Arg Xaa Ile Phe Lys Asp Ala Xaa Arg
Thr Lys Leu Phe Trp)

SEQ ID NO: 5
h-PC(Ala Asn Ser Phe Leu Xaa Xaa Leu Arg His Ser Ser
Leu Xaa Arg Xaa Cys Ile Xaa Xaa Ile Cys Asp Phe
Xaa Xaa Ala Lys Xaa Ile Phe Gln Asn Val Asp Asp
Thr Leu Ala Phe Trp)

SEQ ID NO: 6
h-PS(Ala Asn Ser Leu Leu Xaa Xaa Thr Lys Gln Gly Asn
Leu Xaa Arg Xaa Cys Ile Xaa Xaa Leu Cys Asn Lys
Xaa Xaa Ala Arg Xaa Val Phe Xaa Asn Asp Pro Xaa
Thr Asp Tyr Phe Trp) and SEQ ID NO: 7
h-PZ(Ala Gly Ser Tyr Leu Leu Xaa Xaa Leu Phe Xaa Gly
Asn Leu Xaa Lys Xaa Cys Tyr Xaa Xaa Ile Cys Val
Tyr Xaa Xaa Ala Arg Xaa Val Phe Xaa Asn Asp Xaa
Val Thr Asp Xaa Phe Trp).

The present invention relates to an immunochemical assay wherein a PIVKA of every kind can be determined using an anti-PIVKA-II monoclonal antibody, and to a reagent for such determination.

Specifically, the present invention provides:

(1) a method of determination of a PIVKA of every kind such as PIVKA-VII, -IX, -X, -C, -S and -Z present in an organic specimen according to immunochemical assay, characterized by using an anti-PIVKA-II monoclonal antibody;

(2) a method of determination of a PIVKA of every kind as set forth in (1) above according to the double antibody sandwich method wherein the anti-PIVKA-II monoclonal antibody is used in the form of a solid-supported antibody;

(3) a method of determination of a PIVKA of every kind as set forth in (1) above, wherein the PIVKA of every kind is PIVKA-X;

(4) a method of determination of a PIVKA of every kind as set forth in (1) above, wherein the anti-PIVKA-II monoclonal antibody is MU-3; and (5) a reagent for determination of a PIVKA of every kind, which is used in the foregoing method.

In an immunochemically assaying method for determining PIVKA being present in a specimen of a living body, the invention comprises determining at east one of PIVKA-VII, PIVKA-II, PIVKA-IX, PIVKA-X, PIVKA-C, PIVKA-S and PIVKA-Z with the use of an anti-PIVKA-II monoclonal antibody.

The PIVKA may be selected from PIVKA-VII, PIVKA-IX, PIVKA-X, PIVKA-C, PIVKA-S and PIVKA-Z.

It is preferable that a solid-supported anti-PIVKA-II monoclonal antibody is used as a first antibody and a labeled antibody against a normal protein corresponding to an individual PIVKA to determine is used as a second antibody.

It is preferable in the method that (1) a specimen is introduced into microtiter wells on which an anti-PIVKA-II monoclonal antibody has been immobilized and is reacted; (2) having been washed, the second antibody is added and reacted; and (3) washed, the amount of the labeled antibody is determined.

In a method immunochemically assaying for PIVKA in a specimen of a living body, the reagent of the invention comprises an anti-PIVKA-II monoclonal antibody to determine at least one of PIVKA-VII, PIVKA-II, PIVKA-IX, PIVKA-X, PIVKA-C, PIVKA-S and PIVKA-Z.

The reagent may comprise an anti-PIVKA-II monoclonal antibody, a standard antigen, an enzyme and a substrate.

The present invention will now be described in detail.

The anti PIVKA-II monoclonal antibody to be used is preferably MU-3 as disclosed in EP-B 142 634, which may be prepared according to the following procedure. After the blood plasma of a subject to which a vitamin K antagonist has been administered is salted out with ammonium sulfate, PIVKA-II as an immunizing antigen for production of the monoclonal antibody is purified with DEAE-Sephacel, Heparin-Sepharose and Blue-Sepharose, and further by gel filtration chromatography with Ultrogen AcA44 and prothrombin affinity column chromatography. The other PIVKAs may be prepared according to a customary method as well.

Anti-PIVKA monoclonal antibody-producing hybridoma cells are prepared by immunization of mice with the purified PIVKA, collection of spleen cells thereof, cell fusion thereof with myeloma cell strain P3U1 according to the method of Koehler G. et. al. (Koehler G., Milsrein C., Deviation of specific . antibody-producing culture and tumor lines by cell fusion. Eur. J. Immunol. 1976; 6: 511–9), cloning, a reaction with the PIVKA as an immunizing antigen without a reaction with a normal protein, and subsequent separation of the anti-PIVKA antibody-producing hybridoma cell strain also reactive with other various PIVKAs (an antibody produced by this cell strain will hereinafter he referred to as the "anti-PIVKA monoclonal antibody"). The anti-PIVKA antibody-producing hybridoma cell strain is administered to mice to obtain therefrom ascites, from which IgG can be purified with protein A.

The method of determination of PIVKA of every kind according to the present invention can be carried out according to various immunochemical techniques such as the competitive method, the double antibody sandwich method or the agglutination method, preferably the double antibody sandwich method wherein a solid-supported anti-PIVKA-II monoclonal antibody may be used as the first antibody, while a labeled antibody against a normal protein corresponding to an individual PIVKA as the object of determination may be used as the second antibody. More specifically, use may be made of an antifactor VII antibody as an antibody against a common antigen of PIVKA-VII and factor VII in the case of determination of PIVKA-VII, an antifactor IX antibody as an antibody against a common antigen of PIVKA-IX and factor IX in the case of determination of PIVKA-IX, an antifactor X antibody as an antibody against a common antigen of PIVKA-X and factor X in the case of determination of PIVKA-X, an antiprotein C antibody as an antibody against a common antigen of PIVKA-C and protein C in the case of determination of PIVKA-C, an antiprotein S antibody as an antibody against a common antigen of PIVKA-S and protein S in the case of determination of PIVKA-S, or an antiprotein Z antibody as an antibody against a common antigen of PIVKA-Z and protein Z in the case of determination of PIVKA-Z to determine a PIVKA of every kind in an organic specimen. Further, when a mixture of the above-mentioned second antibodies against the various PIVKAs is used as the second antibody, the total amount of the PIVKAs in an organic specimen can be determined as well.

The second antibody to be used may be any of a polyclonal antibody and a monoclonal antibody. Alternatively, an antibody fragment $F(ab')_2$ or Fab may be used as the antibody in this system of PIVKA determination. Any substance can be used as a substance for labeling the second antibody in so far as it can be quantitatively determined. Examples of the labeling substance include fluorescent substances, radioactive substances, chemiluminescent substances, bioluminescent substances, electrochemiluminescent substances, coloring substances, and enzymes. A solid-phase support that may be used in the case where the first antibody is to be supported may be any support as is commonly used, examples of which include a microtiter plate, plastic beads, erythrocytes, and gelatin particles.

By way of example, the method of determination according to the present invention may be carried out according to the double antibody sandwich method, the procedure of which may be, for example, as follows. Here, the case of an enzyme immunoassay will be described, though it goes without saying that the method of the present invention can also be carried out according to radioimmunoassay or other methods. Specific modes of the reagent for determination according to the present invention are as follows. Specifically, the reagent for determination according to the present invention comprises an anti-PIVKA-II monoclonal antibody as the indispensable component, and may be a set of the anti-PIVKA-II monoclonal antibody (alone or solid-supported) in combination with a member(s) arbitrarily selected from the group consisting of standard antigens, enzymes, and substrates. When a solid phase is contained in the set, the solid phase may arbitrarily be provided in a state of being coated with the anti-PIVKA-II monoclonal antibody. Where an enzyme is contained together with part of an antihuman prothrombin antibody, an antifactor VII antibody, an antifactor IX antibody, an antifactor X antibody, an antiprotein C antibody, an antiprotein S antibody, an antiprotein Z antibody, etc., in the set, both may arbitrarily be provided in a state of conjugation. Both of these embodiments are included in the modes of the reagent for determination according to the present invention. Further, suitable antigen diluent, reaction mixture diluent, solvent for a substrate, liquid reaction terminator, etc., may arbitrarily be added to the set for the convenience of carrying out the determination without limitation of the scope of the present invention.

In carrying out the determination, a standard antigen or an organic specimen may be added to the solid phase coated with the anti-PIVKA monoclonal antibody to effect a reaction. Washing of the solid phase is followed by the addition thereto of the second antibody which is an enzyme-labeled complex of an antiprothrombin antibody as an antibody against a common antigen of PIVKA-II and prothrombin in the case of determination of PIVKA-II, an enzyme-labeled complex of the antifactor VII antibody as the antibody against a common antigen of PIVKA-VII and factor VII in the case of determination of PIVKA-VII, an enzyme-labeled complex of the antifactor IX antibody as the antibody against a common antigen of PIVKA-IX and factor IX in the case of determination of PIVKA-IX, an enzyme-labeled complex of the antifactor X antibody as the antibody against a common antigen of PIVKA-X and factor X in the case of determination of PIVKA-X, an enzyme-labeled complex of the antiprotein C antibody as the antibody against a common antigen of PIVKA-C and protein C in the case of determination of PIVKA-C, an enzyme-labeled complex of the antiprotein S antibody as the antibody against a common antigen of PIVKA-S and protein S in the case of determination of PIVKA-S, or an enzyme-labeled complex of the antiprotein Z antibody as the antibody against a common antigen of PIVKA-Z and protein Z in the case of determination of PIVKA-Z to effect a reaction again; washing; and finally the addition of a substrate to effect a reaction. Thereafter, the amount of the decomposed substrate is determined using a spectro-photometer. As is demonstrated in the following Examples, the reagent for determination according to the present invention enables simple and accurate determination of PIVKA of every kind for the first time.

Use of the anti-PIVKA-II monoclonal antibody enables a simple and accurate determination of PIVKA of every kind.

EXAMPLES

The following Examples will now specifically illustrate the present invention, but should not be construed as limiting the scope of the invention.

Example 1

Purification of PIVKA-II

The blood plasma of the subject to which a vitamin K antagonist had been administered was admixed with the same amount of a 4M saturated solution of ammonium sulfate. The resulting mixture was stirred for 2 hours and centrifuged. The precipitate was dissolved in a 0.1M phosphate buffer solution, followed by dialysis. 0–0.6M NaCl fractionation was effected with DEAE-Sephacel to collect a PIVKA-II fraction, which was dialyzed and then passed through Heparin-Sepharose and Blue-Sepharose. PIVKA-II was further purified by gel filtration chromatography with Ultrogel AcA44 and prothrombin affinity column chromatography.

Example 2

Establishment of Anti-PIVKA-II monoclonal antibody-producing hybridoma cell strain Mice were immunized with 12.5 µg/mouse of the purified PIVKA-II five times. The spleen cells of the immunized mice were collected and subjected to cell fusion with myeloma cell strain P3U1 according to the method of Koehler G. et. al. (Koehler G., Milsrein C., Deviation of specific antibody-producing culture and tumor lines by cell fusion. Eur. J. Immunol. 1976; 511–9), followed by the repetition of cloning three times according to limiting dilution, a reaction with PIVKA-II as the immunizing antigen without a reaction with prothrombin, and subsequent establishment of a cell strain capable of producing a monoclonal antibody reactive with a PIVKA of every kind as an anti-PIVKA-ZZ monoclonal antibody-producing hybridoma cell strain

Example 3

Method of determination

Figure 1:
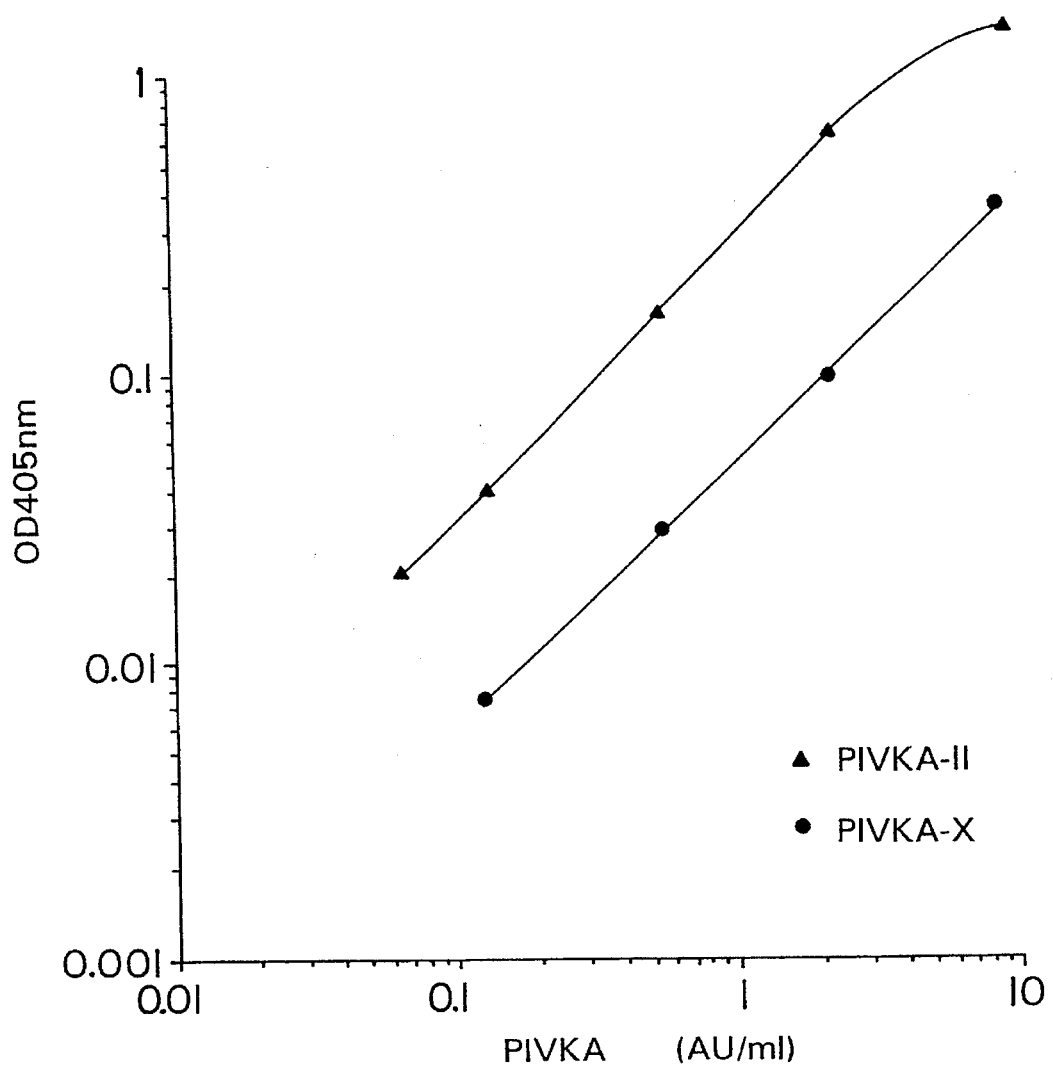
FIG. 1 shows standard curves for PIVKA-II and PIVKA-X determined according to the method of the present invention.
Figure 2:
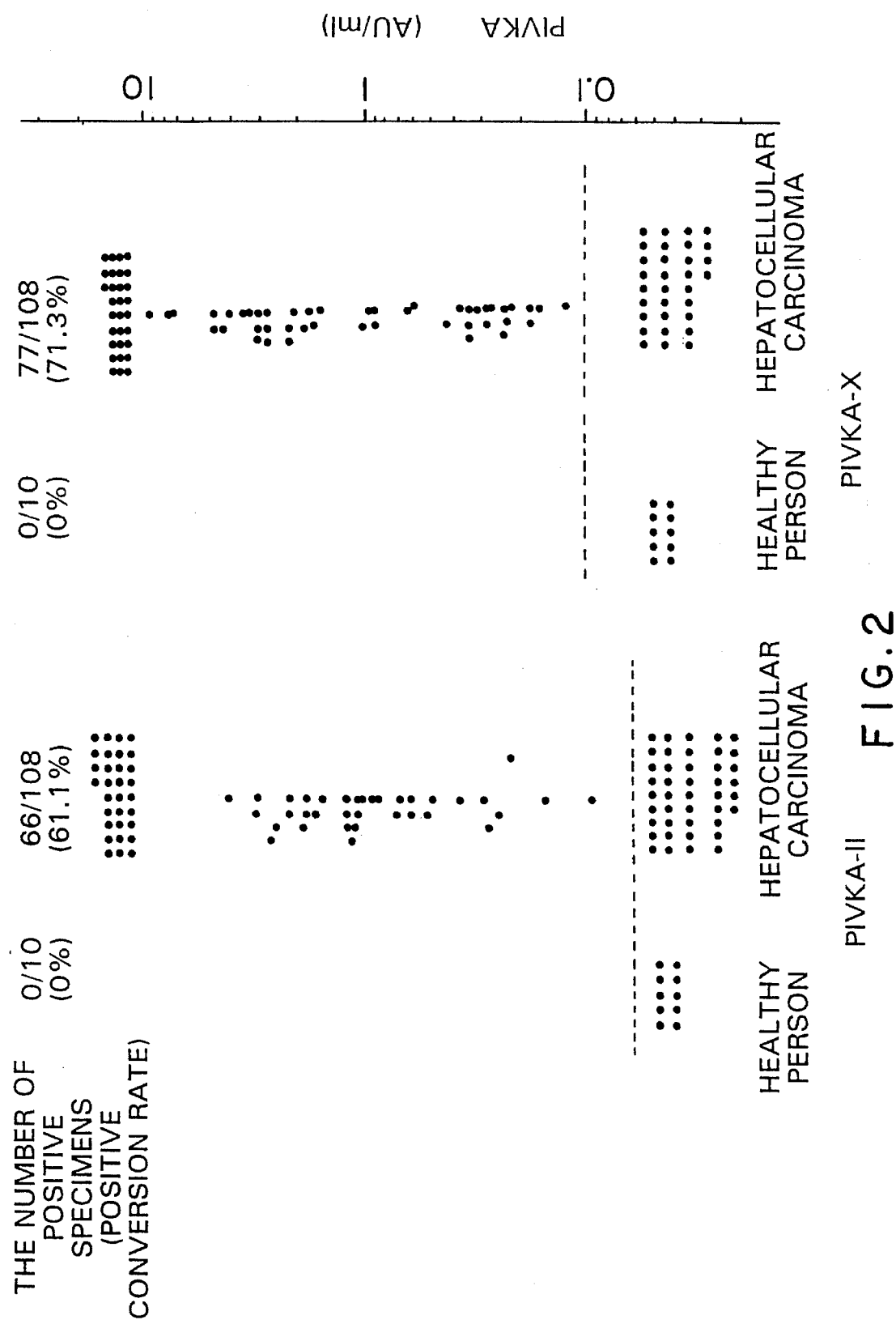
FIG. 2 shows determined values of PIVKA-II and PIVKA-X present in specimens obtained from patients with hepatopathy.

The anti-PIVKA-II monoclonal antibody was solid-supported on a microplate for an enzyme immunoassay according to a customary method as disclosed in EP-B 42 634. 100 µl/well of a specimen was injected into the resulting solid phase coated with the anti-PIVKA monoclonal antibody, followed by one night of a reaction at 4° C. The solid phase was washed three times with a 0.05M Tris hydrochloride buffer solution (0.05% Tween 20) having a pH value of 7.5, followed by the addition thereto of 100 µl of an enzyme-labeled antiprothrombin antibody in the case of determination of PIVKA-II, 100 µl of an enzyme-labeled antifactor VII antibody in the case of determination of PIVKA-VII, 100 of an enzyme-labeled antifactor IX antibody in the case of determination of PIVKA-IX, 100 µl of an enzyme-labeled antifactor X antibody in the case of determination of PIVKA-X, 100 µl of an enzyme-labeled antiprotein C antibody in the case of determination of PIVKA-C, 100 µl of an enzyme-labeled antiprotein S antibody in the case of determination of PIVKA-S, or 100 µl of an enzyme-labeled antiprotein Z antibody in the case of determination of PIVKA-Z to effect a reaction at room temperature for one hour. The solid phase was washed three times with a 0.05M Tris hydrochloride buffer solution (0.054 Tween 20) having a pH value of 7.5, followed by the addition thereto of 100 µl of an ABTS solution, which was then allowed to stand at room temperature for 60 minutes, followed by the addition thereto of 100 µl of a 2mM sodium azide solution to terminate the reaction. The absorbance at a wavelength of 405 nm was measured with a spectrophotometer. Standard curves for PIVKA-II and PIVKA-X determined according to the foregoing procedure are shown in FIG. 1.

Example 4

Determination of PIVKA-II and PIVKA-X present in specimens obtained from patients with hepatopathy and healthy Persons Blood plasma or blood serum specimens collected from 108 patients with hepatopathy and 10 healthy persons were used to determine PIVKA-II and PIVKA-X present therein using the reagent for determination according to the present invention. The results are shown in Table 2. PIVKA-X, which cannot be determined using the conventional reagents for determination, could be determined using the reagent for determination according to the present invention with an increase of 10.2% in positive conversion rate.

As described hereinbefore, use of the anti-PIVKA-II monoclonal antibody as the first antibody and mere exchange of the labeled antibody as the second antibody enable the determination of PIVKA of every kind. Such simple and accurate determinability of the PIVKA of every kind produced in early hepatocellular carcinoma, which has hitherto be incapable of determination, is very useful in diagnosis of hepatocellular carcinoma.

We claim:

1. In a method for immunochemically assaying for PIVKA-X in a specimen of a living body, using a double antibody sandwich method, wherein the improvement comprises:

(a) reacting a solid-supported anti PIVKA-II monoclonal antibody with the specimen to produce a first solid phase;

(b) washing the first solid phase;

(c) reacting a labeled anti-Factor-X antibody with said first solid phase to produce a second solid phase;

(d) washing the second solid phase; and (e) analyzing the second solid phase to determine the amount of the labeled anti-Factor-X that has been connected with the PIVKA-X.

* * * * *

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
        ( A ) LENGTH: 41 amino acids
        ( B ) TYPE: amino acid
        ( C ) TOPOLOGY: linear ( i i ) MOLECULE TYPE: protein ( v i ) ORIGINAL SOURCE:
        ( A ) ORGANISM: Homosapiens ( i x ) FEATURE:
        ( A ) OTHER INFORMATION: Xaa in the sequence is
            γ- carboxylglutamic acid ( x i ) SEQUENCE DESCRIPTION: SEQ ID NO: 1:

```
Ala  Asn  Thr  Phe  Leu  Xaa  Xaa  Val  Arg  Lys  Gly  Asn
 1                                        10

Leu  Xaa  Arg  Xaa  Cys  Val  Xaa  Xaa  Thr  Cys  Ser  Tyr
                                   20

Xaa  Xaa  Ala  Phe  Xaa  Ala  Leu  Xaa  Ser  Ser  Thr  Ala
                         30

Thr  Asp  Val  Phe  Trp
                40
```

( 2 ) INFORMATION FOR SEQ ID NO: 2:

( i ) SEQUENCE CHARACTERISTICS:
        ( A ) LENGTH: 41 amino acids
        ( B ) TYPE: amino acid
        ( C ) TOPOLOGY: linear ( i i ) MOLECULE TYPE: protein ( v i ) ORIGINAL SOURCE:
        ( A ) ORGANISM: Homosapiens ( i x ) FEATURE:
        ( A ) OTHER INFORMATION: Xaa in the sequence is
            γ- carboxylglutamic acid ( x i ) SEQUENCE DESCRIPTION: SEQ ID NO: 2:

```
Ala  Asn  Ser  Phe  Leu  Xaa  Xaa  Met  Lys  Lys  Gly  His
 1                                        10

Leu  Xaa  Arg  Xaa  Cys  Met  Xaa  Xaa  Thr  Cys  Ser  Tyr
                                   20

Xaa  Xaa  Ala  Arg  Xaa  Val  Phe  Xaa  Asp  Ser  Asp  Lys
                         30

Thr  Asn  Xaa  Phe  Trp
                40
```

( 2 ) INFORMATION FOR SEQ ID NO: 3:

( i ) SEQUENCE CHARACTERISTICS:
        ( A ) LENGTH: 42 amino acids
        ( B ) TYPE: amino acid ( C ) TOPOLOGY: linear ( i i ) MOLECULE TYPE: protein ( v i ) ORIGINAL SOURCE:
    ( A ) ORGANISM: Homosapiens ( i x ) FEATURE:
    ( A ) OTHER INFORMATION: Xaa in the sequence is
        γ- carboxylglutamic acid ( x i ) SEQUENCE DESCRIPTION: SEQ ID NO: 3:

```
Tyr  Asn  Ser  Gly  Lys  Leu  Xaa  Xaa  Phe  Val  Gln  Gly
 1                                            10

Asn  Leu  Xaa  Arg  Xaa  Cys  Met  Xaa  Xaa  Lys  Cys  Ser
                              20

Phe  Xaa  Xaa  Ala  Arg  Xaa  Val  Glu  Xaa  Asn  Thr  Xaa
                    30

Lys  Thr  Thr  Xaa  Phe  Trp
               40
```

( 2 ) INFORMATION FOR SEQ ID NO: 4:

( i ) SEQUENCE CHARACTERISTICS:
        ( A ) LENGTH: 41 amino acids
        ( B ) TYPE: amino acid
        ( C ) TOPOLOGY: linear ( i i ) MOLECULE TYPE: protein ( v i ) ORIGINAL SOURCE:
        ( A ) ORGANISM: Homosapiens ( i x ) FEATURE:
        ( A ) OTHER INFORMATION: Xaa in the sequence is
            γ- carboxylglutamic acid ( x i ) SEQUENCE DESCRIPTION: SEQ ID NO: 4:

```
Ala  Asn  Ala  Phe  Leu  Xaa  Xaa  Leu  Arg  Pro  Gly  Ser
 1                                            10

Leu  Xaa  Arg  Xaa  Cys  Lys  Xaa  Xaa  Gln  Cys  Ser  Phe
                              20

Xaa  Xaa  Ala  Arg  Xaa  Ile  Phe  Lys  Asp  Ala  Xaa  Arg
                    30

Thr  Lys  Leu  Phe  Trp
               40
```

( 2 ) INFORMATION FOR SEQ ID NO: 5:

( i ) SEQUENCE CHARACTERISTICS:
        ( A ) LENGTH: 41 amino acids
        ( B ) TYPE: amino acid
        ( C ) TOPOLOGY: linear ( i i ) MOLECULE TYPE: protein ( v i ) ORIGINAL SOURCE:
        ( A ) ORGANISM: Homosapiens ( i x ) FEATURE:
        ( A ) OTHER INFORMATION: Xaa in the sequence is
            γ- carboxylglutamic acid ( x i ) SEQUENCE DESCRIPTION: SEQ ID NO: 5:

```
Ala  Asn  Ser  Phe  Leu  Xaa  Xaa  Leu  Arg  His  Ser  Ser
 1                                            10

Leu  Xaa  Arg  Xaa  Cys  Ile  Xaa  Xaa  Ile  Cys  Asp  Phe
                         20
```

```
Xaa  Xaa  Ala  Lys  Xaa  Ile  Phe  Gln  Asn  Val  Asp  Asp
                         30

Thr  Leu  Ala  Phe  Trp
               40
```

( 2 ) INFORMATION FOR SEQ ID NO: 6:

( i ) SEQUENCE CHARACTERISTICS:
        ( A ) LENGTH: 41 amino acids
        ( B ) TYPE: amino acid
        ( C ) TOPOLOGY: linear ( i i ) MOLECULE TYPE: protein ( v i ) ORIGINAL SOURCE:
        ( A ) ORGANISM: Homosapiens ( i x ) FEATURE:
        ( A ) OTHER INFORMATION: Xaa in the sequence is
            γ- carboxylglutamic acid ( x i ) SEQUENCE DESCRIPTION: SEQ ID NO: 6:

```
Ala  Asn  Ser  Leu  Leu  Xaa  Xaa  Thr  Lys  Gln  Gly  Asn
 1                                            10

Leu  Xaa  Arg  Xaa  Cys  Ile  Xaa  Xaa  Leu  Cys  Asn  Lys
                              20

Xaa  Xaa  Ala  Arg  Xaa  Val  Phe  Xaa  Asn  Asp  Pro  Xaa
                    30

Thr  Asp  Tyr  Phe  Trp
               40
```

( 2 ) INFORMATION FOR SEQ ID NO: 7:

( i ) SEQUENCE CHARACTERISTICS:
        ( A ) LENGTH: 42 amino acids
        ( B ) TYPE: amino acid
        ( C ) TOPOLOGY: linear ( i i ) MOLECULE TYPE: protein ( v i ) ORIGINAL SOURCE:
        ( A ) ORGANISM: Homosapiens ( i x ) FEATURE:
        ( A ) OTHER INFORMATION: Xaa in the sequence is
            γ- carboxylglutamic acid ( x i ) SEQUENCE DESCRIPTION: SEQ ID NO: 7:

```
Ala  Gly  Ser  Tyr  Leu  Leu  Xaa  Xaa  Leu  Phe  Xaa  Gly
 1                                            10

Asn  Leu  Xaa  Lys  Xaa  Cys  Tyr  Xaa  Xaa  Ile  Cys  Val
                              20

Tyr  Xaa  Xaa  Ala  Arg  Xaa  Val  Phe  Xaa  Asn  Asp  Xaa
                    30

Val  Thr  Asp  Xaa  Phe  Trp
               40
```